United States Patent [19]
Nolan et al.

[11] Patent Number: 5,776,150
[45] Date of Patent: Jul. 7, 1998

[54] SUTURE ASSIST DEVICE

[75] Inventors: Leo J. Nolan; John P. Measamer, both of Cincinnati; James D. Staley, Jr., Loveland; Robert F. Welch, Maineville, all of Ohio

[73] Assignee: Ethicon Endo Surgery, Inc., Cincinnati, Ohio

[21] Appl. No.: 662,755

[22] Filed: Jun. 10, 1996

[51] Int. Cl.$^6$ ................................................ A61B 17/04
[52] U.S. Cl. ........................ 606/148; 606/139; 606/147
[58] Field of Search ............................ 606/148, 144, 606/147, 145, 139

[56] References Cited

U.S. PATENT DOCUMENTS

| | | | |
|---|---|---|---|
| 5,234,443 | 8/1993 | Phan et al. | 606/148 |
| 5,250,054 | 10/1993 | Li | 606/148 |
| 5,281,237 | 1/1994 | Gimpelson | 606/144 |
| 5,318,579 | 6/1994 | Chow | 606/148 |
| 5,383,877 | 1/1995 | Clarke | 606/148 |
| 5,449,367 | 9/1995 | Kadry | 606/139 |
| 5,496,335 | 3/1996 | Thomason et al. | 606/148 |
| 5,507,758 | 4/1996 | Thomason et al. | 606/148 |

OTHER PUBLICATIONS

"Ojigi Tying Spatula: A Newly Developed Movable Spatula for Laparoscopic Ligation" Daijo Hashimoto, Sarder Abdun Nayeem, Shuji Kajiwara, Takanobu Hoshino, and Tsuneo Fukuyo *Surgical Laparoscopy & Endoscopy,* vol. 3, No. 6, pp. 459–461. © 1993 Raven Press, Ltd., New York.

*Primary Examiner*—Gary Jackson
*Attorney, Agent, or Firm*—Bernard Shay

[57] ABSTRACT

A surgical instrument including a handle, an end effector including jaws, an elongated tube connecting the handle to the end effector, a connector within the tube connecting the handle to the jaw members; and a first slot in the first jaw and a second slot in the jaw wherein the first and second slots are arranged such that only a portion of the slots overlap when the first and second jaws are closed to create a hole in the jaw which may be used for positioning a suture in the tissue. The first slot in the first jaw extends to a side of the first jaw and the second slot in the second jaw extends to a side of the second jaw creating pathways for removing the suture when the jaws are opened. The surgical instrument may also include a retractable tying pin adjacent the end effector and a knot pusher at the distal end of the end effector. A method of using the surgical instrument described above includes closing the first and second jaws on tissue; passing a surgical needle with a suture attached thereto through the overlapping portion of the first and second slots; opening the first and second jaws and releasing the suture by passing the suture through the first and the second slots.

21 Claims, 7 Drawing Sheets

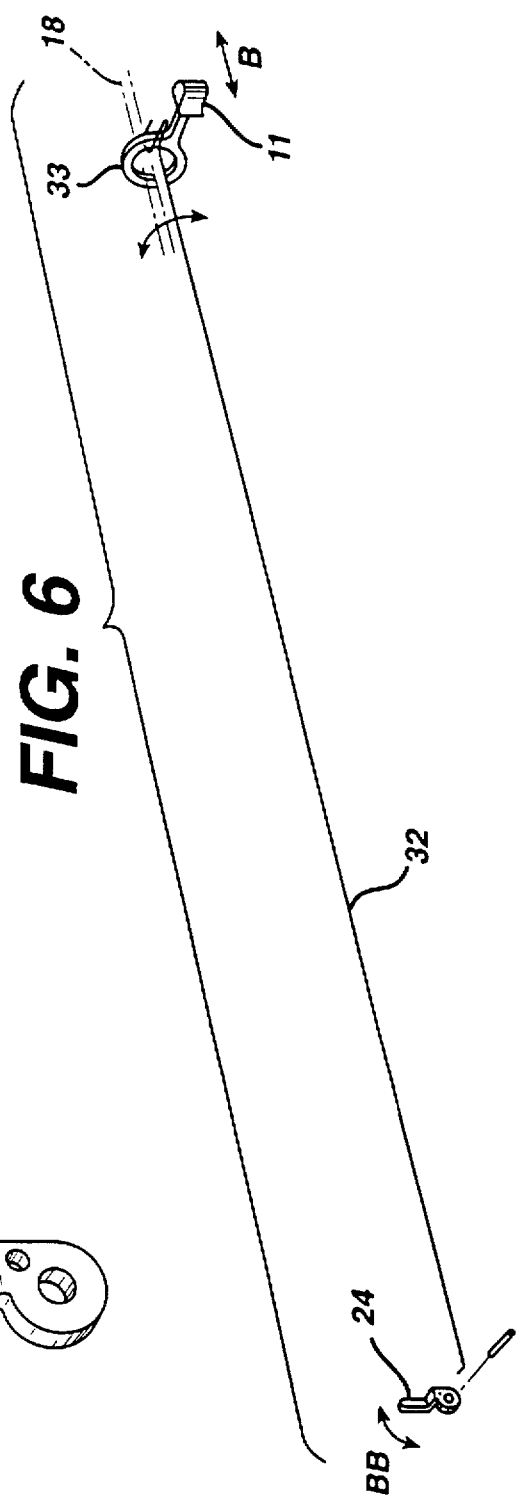
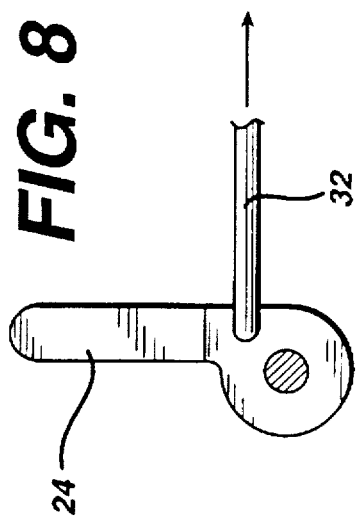
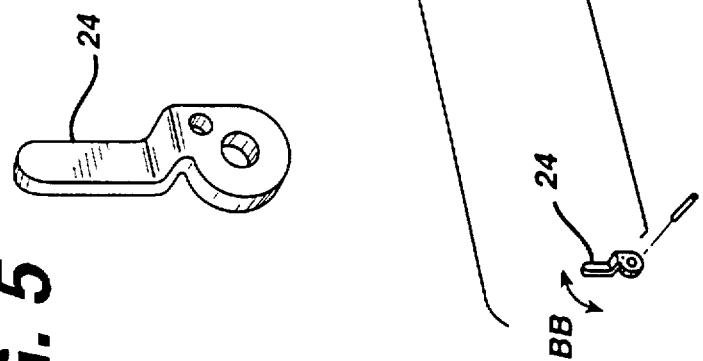
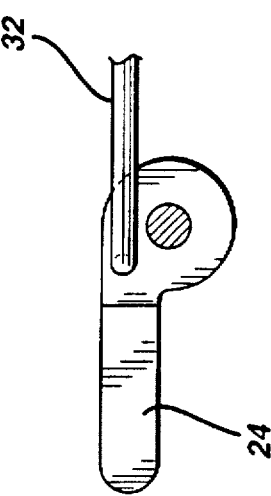

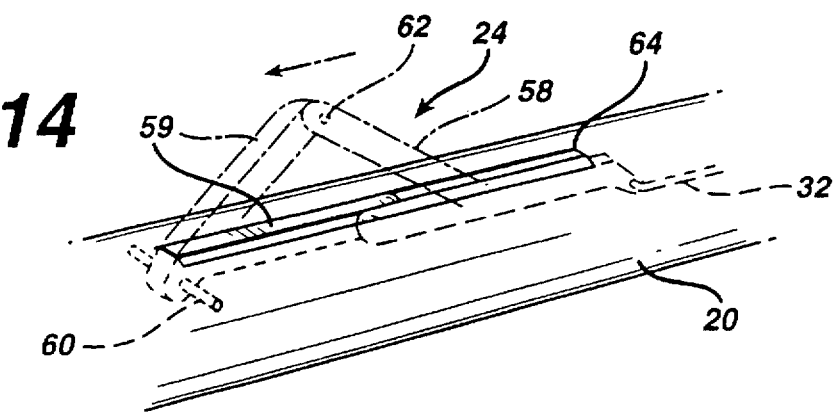
FIG. 14
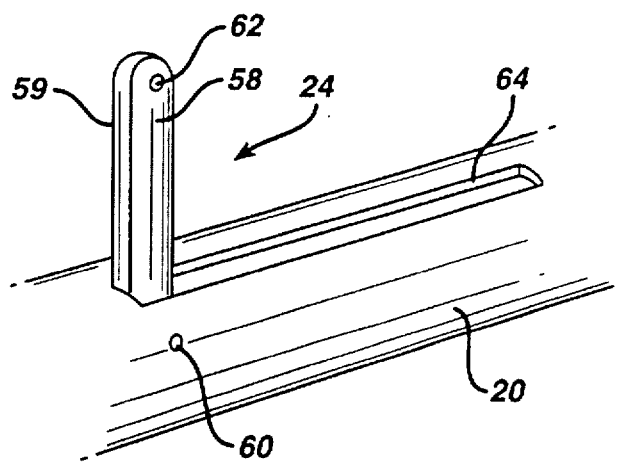
FIG. 15
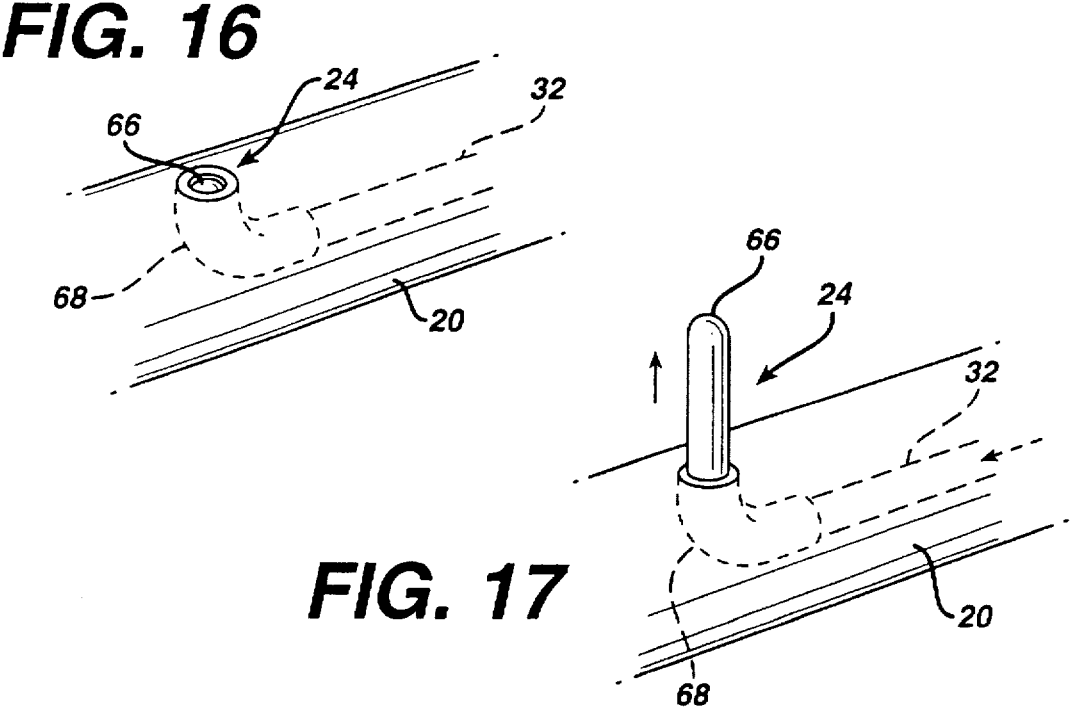
FIG. 16
FIG. 17

SUTURE ASSIST DEVICE

FIELD OF THE INVENTION

The present invention relates, in general, to an improved surgical instrument and, more particularly, to a grasper including an opening in the grasper jaws for use in positioning a surgical needle and suture in tissue.

BACKGROUND OF THE INVENTION

In many surgical operations, including both open and minimally invasive operations, surgeons must use sutures to join tissue. Accurately positioning surgical needles is, at times, difficult. Accurately positioning surgical needles is particularly important where a grasper or other instrument is used to stabilize or to hold tissue layers prior to placing the needle. In order to enhance a surgeon's ability to position a needle in tissue, it would be advantageous to design a grasper which includes an opening in the jaws which opening may be used to position a surgical needle. When using such a device, the grasper would be used to grasp and hold one or more layers of tissue. The surgical needle could then be passed through the grasper jaws and the tissue layer(s). However, once the needle has been passed through the grasper jaws it is difficult to remove the suture from the opening in the jaws. Therefore, it would be advantageous to design an instrument such as a grasper including an opening in the jaws wherein the suture could be easily removed when the jaws are opened. Once the suture is placed, a knot may be tied in the suture. Once the knot is tied, it must be pushed against the tissue and tightened. Once the knot is pushed against the tissue, it may be held in place by flattening the knot. Thus, it would be further advantageous to design a grasper as described including a knot tying post wherein the knot, once tied, could be pushed against the tissue and flattened.

SUMMARY OF THE INVENTION

A surgical instrument including a proximal end and a distal end, a handle comprising first and second gripping members at the proximal end of the instrument, an end effector comprising first and second jaw members, an elongated tube connecting the handle to the end effector, a connector within the tube connecting at least one of the gripping members to the jaw members; and a first slot in the first jaw member and a second slot in the second jaw member wherein the first and second slots are arranged such that only a portion of the slots overlap when the first and second jaws are closed. In one embodiment of a surgical instrument according to the present invention, the first slot in the first jaw extends to a side of the first jaw and the second slot in the second jaw extends to a side of the second jaw. A surgical instrument according to the present invention may further include a retractable tying pin adjacent the end effector wherein a trigger is attached to the retractable tying pin through the tube. The end effector may also include a knot pusher which may comprise notches in the distal end of the first and second jaw members. In an alternate embodiment of the present invention, the tying pin may be formed of a flexible material such as Nylon wire or other suitable material which may be extended and retracted through a guide tube or slot.

The present invention further includes a method of using a surgical instrument including an end effector comprising first and second jaw members wherein the first jaw member includes a first slot and the second jaw member includes a second slot and wherein the first and second slots are arranged such that only a portion of the first and second slots overlap when the first and second jaws are closed. The method according to the present invention comprising the steps of: closing the first and second jaws on tissue; passing a surgical needle with a suture attached thereto through the tissue by passing the needle and suture through the overlapping portion of the first and second slots; opening the first and second jaws and releasing the suture by passing the suture through the non overlapping portion of the first and the second slots. The method according to the present invention may further include the steps of twisting one end of a portion of the suture around the instrument to create at least one suture loop, grasping the other end of the suture and pulling the suture through the at least one loop.

In a surgical instrument as described above and further including a retractable tying pin, the method according to the present invention may also include the steps of: extending a tying pin prior to creating the suture loop; and retracting the tying pin prior to pulling the suture through the loop to create a knot in the suture. The tying pin is retracted to allow the suture loop to be freely removed from the instrument.

In a surgical instrument as described above and further including a knot pusher comprised of one or more notches in the jaws of the end effector, the method according to the present invention may also include the steps of closing the jaws of the end effector to form the knot pusher; placing the knot in the knot pusher; forcing the knot against the tissue; and, opening the end effector jaws to flatten the knot against the tissue.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 5 is a perspective view of one embodiment of a tying pin for use in a surgical instrument according to the present invention.

FIG. 6 is a perspective view of one embodiment of the connection between the tying pin and the tying pin trigger for use in a surgical instrument according to the present invention.

FIG. 7 is a side view of the tying pin illustrated in FIG. 5 in a retracted position.

FIG. 8 is a side view of the tying pin illustrated in FIG. 5 in an extended position.

FIG. 14 is a perspective view of one embodiment of a retractable tying pin for use in a surgical instrument according to the present invention in its partially extended position.

FIG. 15 is a perspective view of the retractable tying pin of FIG. 14 in its fully extended position.

FIG. 16 is a perspective view of one embodiment of a retractable tying pin for use in a surgical instrument according to the present invention in its retracted position.

FIG. 17 is a perspective view of the retractable tying pin illustrated in FIG. 16 in its fully extended position.

DETAILED DESCRIPTION OF THE INVENTION

Figure 1:
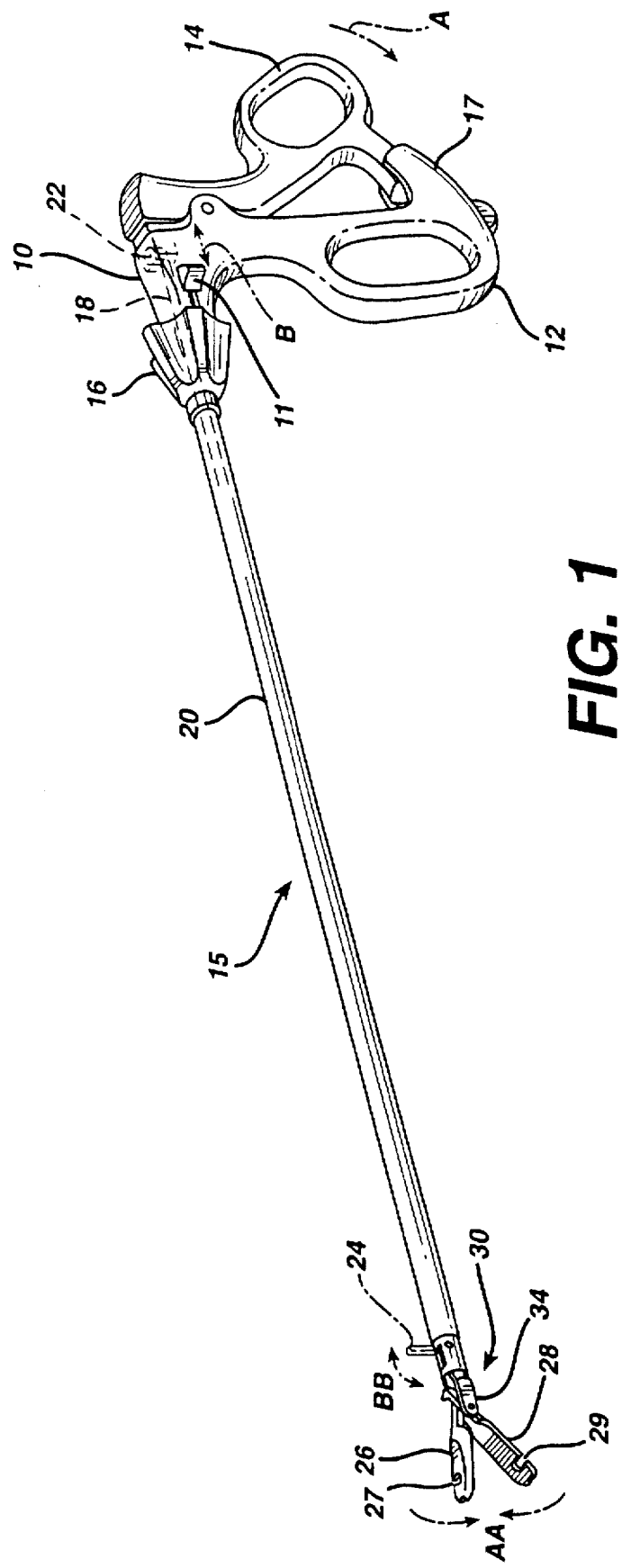
FIG. 1 is a perspective drawing of a surgical instrument according to one embodiment of the present invention.

FIG. 1 is a perspective drawing of a surgical instrument 15 which may be referred to as a "grasper". In FIG. 1, handle 10 includes first grip member 12, second grip member 14, tying pin trigger 11 and connector 22. Connector 22 may be, for example a ball and joint connector. Elongated hollow tube 20 is connected to handle 10 by rotation knob 16. End effector 30 is connected to handle 10 and second grip member 14 by jaw actuator 18 which passes through tube 20 to connector 22 on grip member 14. As illustrated in FIG. 6, tying pin trigger 11 is connected to retractable tying pin 24 by tying pin connector 32 which passes through tube 20. End effector 30 includes first jaw 26 and second jaw 28. First jaw 26 includes slot 27. Second jaw 28 includes slot 29. Handle 10 may also include a 10 conventional releasable ratchet mechanism 17 to assist the surgeon in grasping and holding tissue.

In FIG. 1, movement of second grip member 14 relative to first grip member 12 is translated to end effector 30 by connector 22 and jaw actuator 18. Thus, when second grip member 14 is moved in direction A, jaw members 26 and 28 close along path AA. Trigger 11 is connected to tying pin 24 as illustrated in FIG. 6, therefore, moving trigger 11 in direction B extends and retracts tying pin 24 along path BB. End effector 30, being attached to tube 20 by support members 34, rotates with respect to handle 10 when rotation knob 16 is turned.

Figure 2:
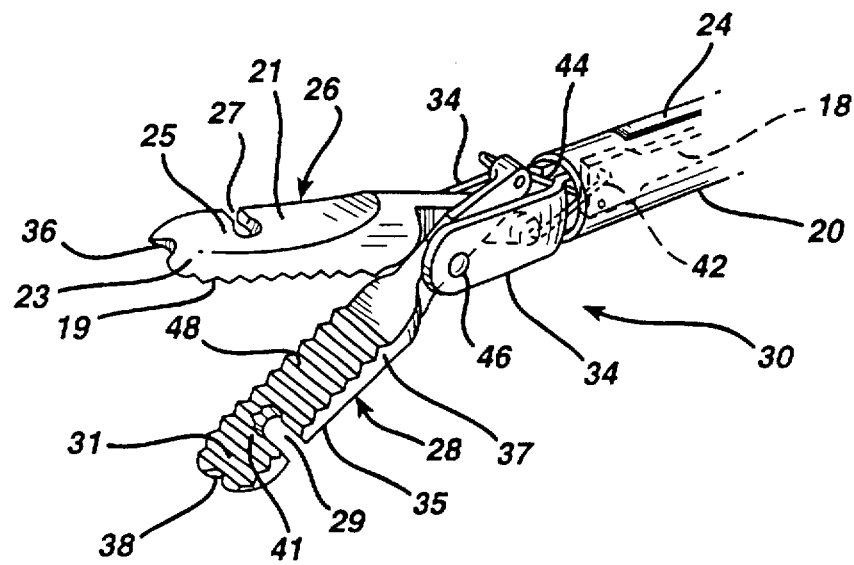
FIG. 2 is a perspective drawing of an end effector according to one embodiment of the present invention.
Figure 4:
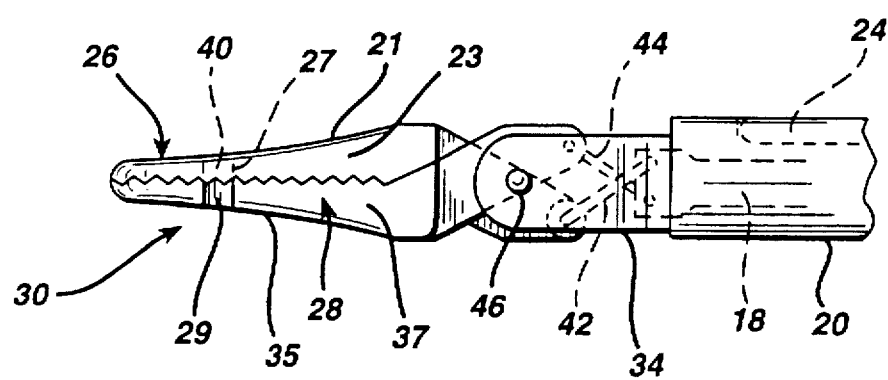
FIG. 4 is a side view of the end effector illustrated in FIGS. 2 and 3.

FIG. 2 is a perspective drawing of an end effector according to one embodiment of the present invention. In FIG. 2, end effector 30 is open with jaws 26 and 28 separated to receive tissue. Tube 20 includes movable jaw actuator 18 which is attached to jaws 26 and 28 through connector rods 42 and 44 respectively. Jaw 26 includes slot 27 and notch 36. Notch 36 is formed in the distal end of jaw 26. Jaw 26 further includes tissue grasping surface 19 and external surface 21. The intersection of tissue grasping surface 19 and external surface 21 forms outside edge 23. Slot 27 extends through jaw 26 from external surface 21 to tissue grasping surface 19 and from a central region 25 of jaw 26 to outside edge 23. Jaw 28 includes slot 29 and notch 38. Notch 38 is formed in the distal end of jaw 28. Jaw 28 further includes tissue grasping surface 31 and external surface 35. The intersection of tissue grasping surface 31 and external surface 35 forms outside edge 37. Slot 29 extends through jaw 28 from external surface 35 to tissue grasping surface 31 and from a central region 41 of jaw 28 to outside edge 37. Jaws 26 and 28 are adapted to pivot around pivot pin 46 in response to forces applied by jaw actuator 18 through connector rods 42 and 44. Thus, when jaw actuator 18 is moved distally, connector rods 42 and 44 force jaws 26 and 28, respectively, to pivot around pivot pin 46, opening end effector 30 as illustrated in FIG. 2. When jaw actuator 18 is moved proximally, connector rods 42 and 44 force jaws 26 and 28, respectively, to pivot around pivot pin 46, closing end effector 30 as illustrated in FIG. 4. First jaw 26 and second jaw 28 include ridges 48 which assist in gripping tissue when jaws 26 and 28 are closed. Jaw support members 34 connect jaws 26 and 28 to tube 20 through pivot pin 46.

Figure 3:
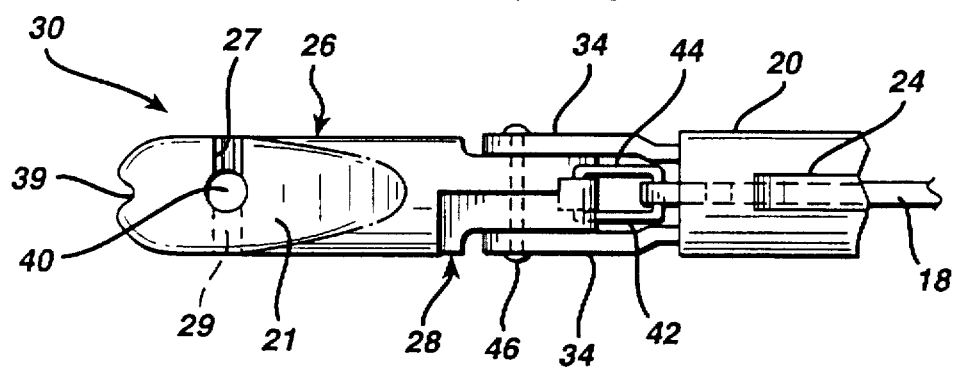
FIG. 3 is a top view of the end effector illustrated in FIG. 2.

FIG. 3 is a top view of the end effector illustrated in FIG. 2. In FIG. 3, jaws 26 and 28 are closed. When closed, a portion of slot 27 overlaps with a portion of slot 29, creating needle opening 40 which extends through end effector 30. Opening 40 is generally large enough to pass a surgical needle and suture. FIG. 4 is a side view of the closed end effector illustrated in FIG. 3. As illustrated in FIG. 4, when jaws 26 and 28 are closed, needle opening 40 passes through end effector 30 from external surface 21 to external surface 35.

Figure 11:
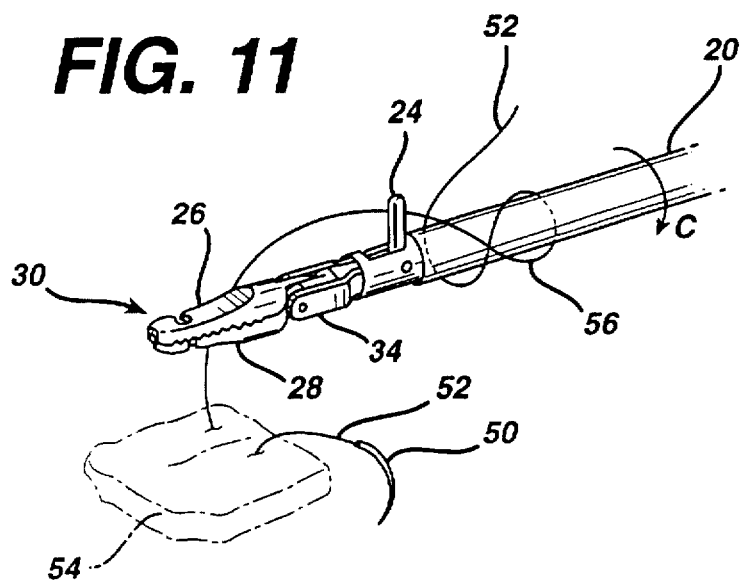
FIG. 11 illustrates a third step in a method of tying a suture knot using an instrument according to the present invention, wherein the suture is wound around the instrument shaft.

FIG. 5 is a perspective view of a tying pin for use in a surgical instrument according to the present invention. Tying pin 24 may be extended to assist in forming suture loops as illustrated in FIG. 11. FIG. 6 is a perspective view of the connection between tying pin 24, tying pin trigger 11 and tying pin connector 32. Rotation coupler 33 in FIG. 6 which is part of tying pin connector 32 is adapted to transmit longitudinal motion from trigger 11 to pin 24 without restraining pin 24 from rotating cooperatively with end effector 30 when, for example, tube 20 is rotated to position end effector 30. As illustrated in FIG. 7, moving trigger 11 and, thus, tying pin connector 32 distally, moves tying pin 24 into a retracted position. As illustrated in FIG. 8, moving trigger 11 and, thus, tying pin connector 32 proximally, moves tying pin 24 into an extended position.

Figure 9:
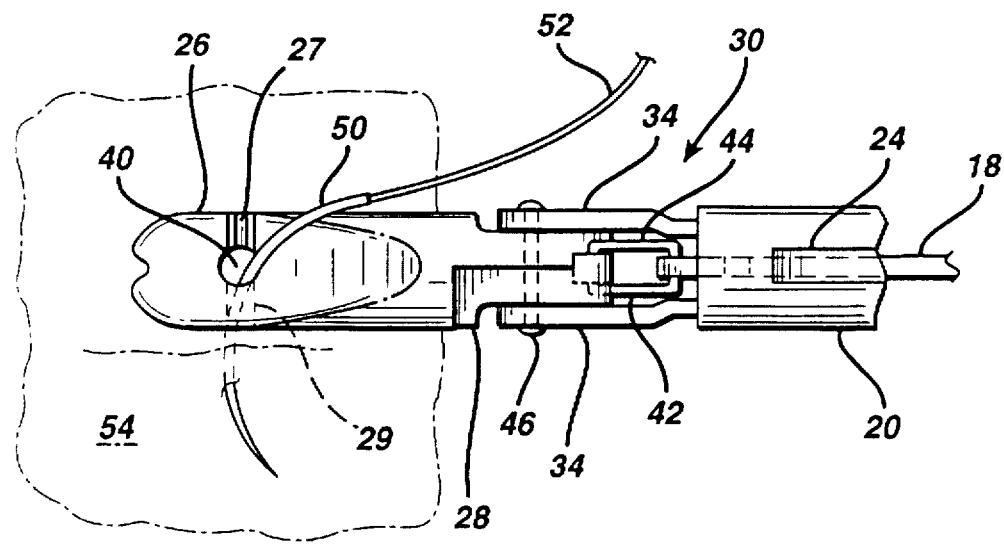
FIG. 9 illustrates a first step in a method of tying a suture knot using an instrument according to the present invention wherein the suture is passed through an opening in the end effector jaws.
Figure 10:
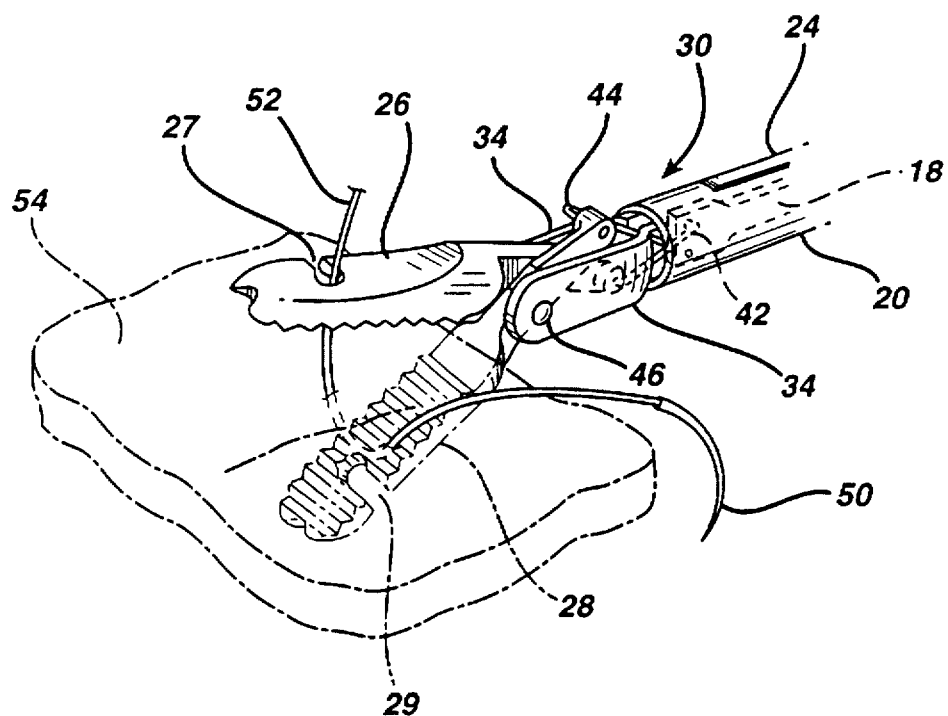
FIG. 10 illustrates a second step in a method of tying a suture knot using an instrument according to the present invention wherein the jaws are opened to release the suture.
Figure 12:
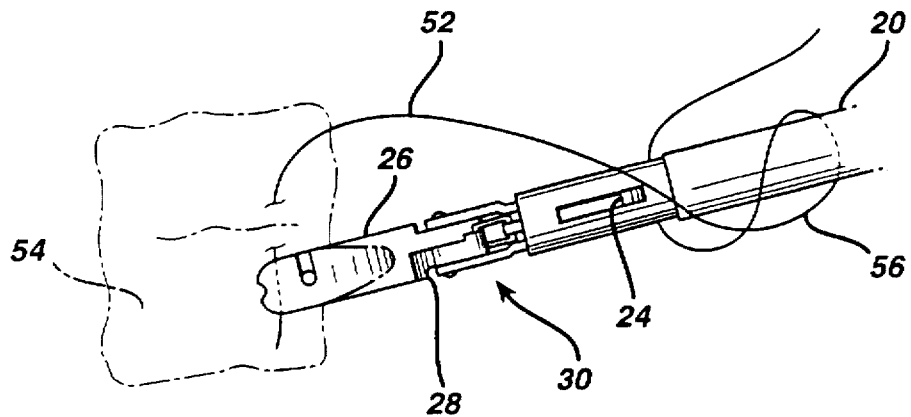
FIG. 12 illustrates a fourth step in a method of tying a suture knot using an instrument according to the present invention wherein the suture is grasped by the end effector.
Figure 13:
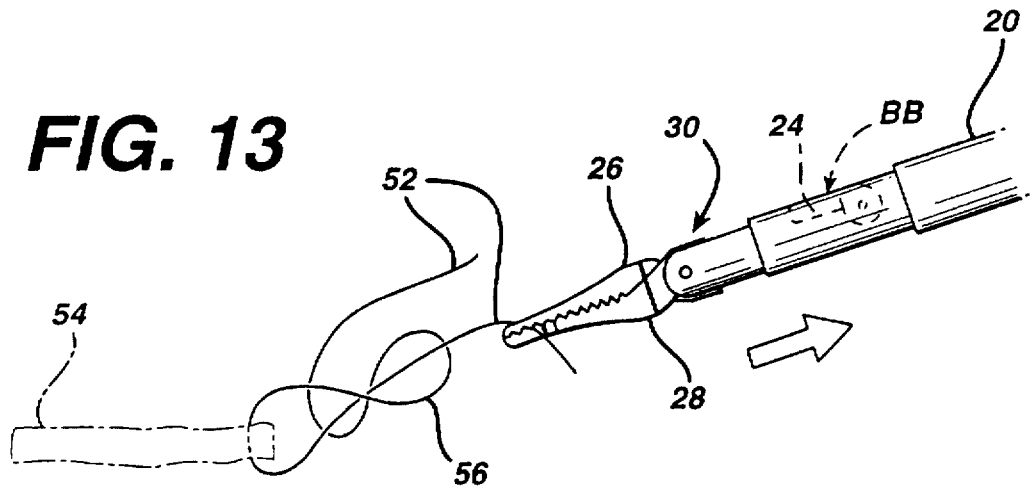
FIG. 13 illustrates a fifth step in a method of tying a suture knot using an instrument according to the present invention wherein the tying pin is retracted and the suture and needle are pulled through the loops created by winding the suture around the instrument shaft.

FIG. 9 illustrates a first step in a method of tying a suture knot using an instrument according to the present invention. In FIG. 9, tissue 54 is grasped between jaws 26 and 28 of end effector 30. Needle 50 and suture 52 are passed through needle opening 40 and tissue 54. FIG. 10 illustrates a second step in a method of tying a suture knot using an instrument according to the present invention. After surgical needle 50 and suture 52 are passed through tissue 54, end effector 30 may be opened, opening jaws 26 and 28. Once jaws 26 and 28 are opened, suture 52 may be removed from needle opening 40 through slots 27 and 29. FIG. 11 illustrates a third step in a method of tying a suture knot using an instrument according to the present invention. In FIG. 11, tying pin 24 is extended and suture 52 is wound around hollow tube 20 by, for example, turning tube 20 in direction C to create one or more suture loops 56. FIG. 12 illustrates a fourth step in a method of tying a suture knot using an instrument according to the present invention. In FIG. 12, needle 50 is removed and suture 52 is grasped by end effector 30 as illustrated. Once grasped, suture 52 may be pulled through suture loops 56 as illustrated in FIG. 13. FIG.

13 illustrates a fifth step in a method of tying a suture knot using an instrument according to the present invention wherein tying pin 24 is retracted the suture 52 is pulled through suture loops 56 to tie a surgical knot.

FIGS. 14 and 15 illustrate an alternate embodiment of a tying pin according to the present invention. As illustrated in FIGS. 1–13, tying pin 24 comprises a single element which is extended and retracted by moving tying pin connector 32 as illustrated in FIGS. 5–8. In FIGS. 14 and 15, tying pin 24 comprises tying pin element 58 and tying pin element 59 which are connected by pivot pin 62. Tying pin element 58 is pivotally connected to tying pin connector 32, while tying pin element 59 is pivotally connected to pivot pin 60 such that distal movement of tying pin connector 32 forces tying pin elements 58 and 59 up and out of tying pin slot 64 as illustrated in FIG. 14. In FIG. 15 tying rod 24 is in its fully extended position with tying rod elements 58 and 59 forming tying rod element 24.

FIGS. 16 and 17 illustrate a further alternate embodiment of a tying pin according to the present invention. In FIG. 16, tying pin 24 comprises a flexible rod 66 which may be made of, for example Nylon wire or other suitable material. Flexible rod 66 is sufficiently rigid to provide a stop for sutures 52 when forming suture loops 56. In the embodiment of FIGS. 16 and 17, tying pin connector 32 may be, for example, an extension of flexible rod 66. In this embodiment, support 68 acts to change the direction of motion of flexible rod 66. Therefore, moving tying pin connector 32 in a distal direction will extend flexible rod 66 to form tying rod 24. Alternatively, moving tying pin connector 32 in a proximal direction will retract flexible rod 66, retracting tying rod 24.

Figure 18:
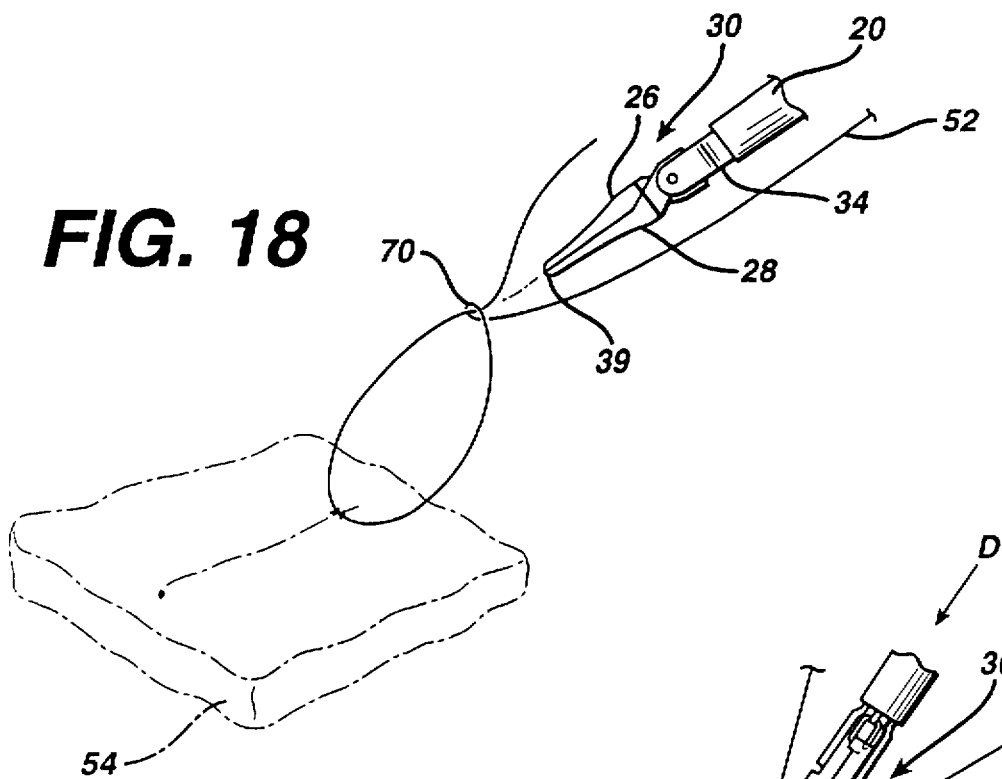
FIG. 18 illustrates a method of pushing a suture knot using a knot pusher in a surgical instrument according to one embodiment of the present invention.
Figure 19:
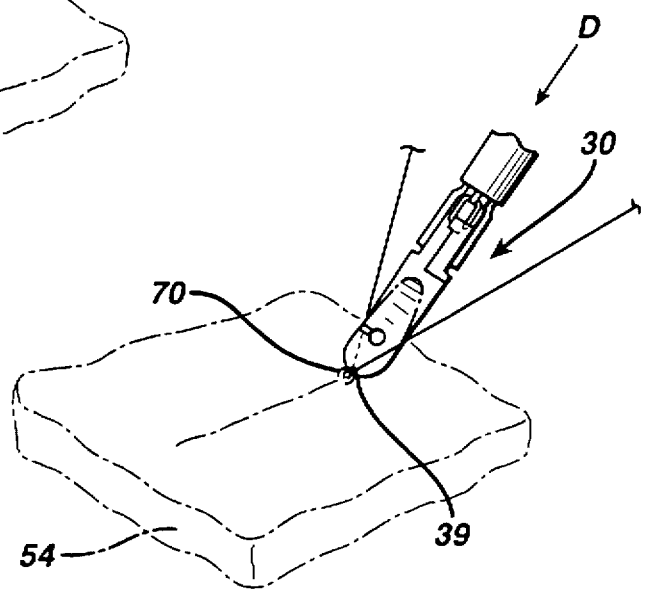
FIG. 19 illustrates a further step in the method illustrated in FIG. 18.
Figure 20:
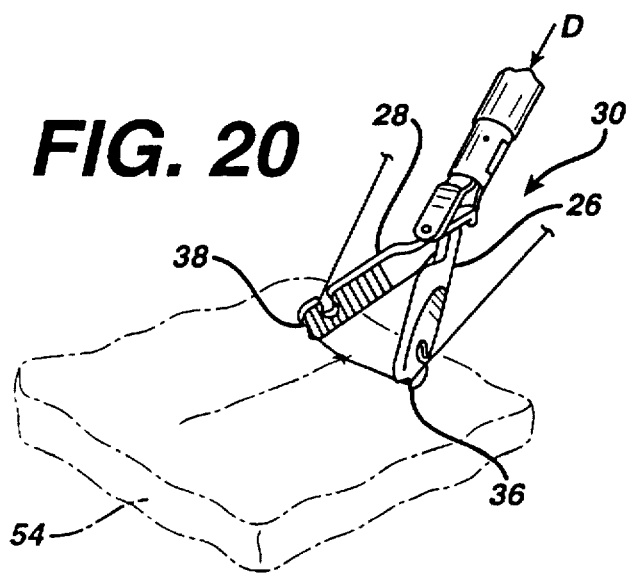
FIG. 20 illustrates a further step in the method according to the present invention.

FIGS. 18 and 19 illustrate a method of tying off a knot using the notches in the end effector according to one embodiment of the present invention. When end effector 30 is closed, notches 36 and 38 form knot pusher 39. Once knot 70 is formed, for example as illustrated in FIGS. 9–13, pusher 39 may be placed against knot 70 and used to force knot 70 against tissue 54. As illustrated in FIG. 20, knot 70 may then be flattened by opening jaws 26 and 28 while maintaining pressure on knot 70.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An end effector for a surgical instrument, said end effector comprising:
   a first jaw including a first hole and a first slot;
   a second jaw including a second hole and a second slot, said second jaw being pivotally connected to said first jaw wherein said first hole is aligned with said second hole when said first and second jaw are closed;
   a first connector connected to said first jaw such that movement of said first connector moves said first jaw from a first open position to a second, closed position; and
   a second connector connected to said second jaw such that movement of said second connector moves said second jaw from a first open position to a second, closed position.

2. An end effector according to claim 1 wherein said first slot in said first jaw extends from said first hole to a first side of said first jaw and said second slot in said second jaw extends from said second hole to a second side of said second jaw.

3. An end effector according to claim 2 wherein said first slot is not aligned with said second slot when said first and second jaws are closed.

4. An end effector according to claim 3 wherein said first jaw includes a first notch at a distal end of said first jaw and said second jaw includes a second notch at a distal end of said second jaw and wherein said first and second notches are aligned when said jaws are closed.

5. An end effector for use in a surgical instrument, said end effector comprising:
   a first jaw member including a first slot extending to one side of said first jaw member;
   a second jaw member opposed to said first jaw member including a second slot extending to one side of said second jaw member;
   a pivot point wherein said first and said second jaw members pivot around said pivot point such that at least a portion of said first and said second jaw members overlap when said jaw members are closed;
   an opening extending through said first and said second jaw members when said jaw members are closed wherein said opening comprises a portion of said first slot and a portion of said second slot.

6. An end effector according to claim 5 wherein said first slot extends from a central portion of said first jaw to a side of said first jaw and said second slot extends from a central portion of said second jaw to a side of said second jaw.

7. An end effector according to claim 6 wherein said end effector further includes a retractable tying post at a proximal end of said end effector.

8. An end effector according to claim 7 wherein said retractable tying post comprises a flexible rod.

9. An end effector according to claim 7 wherein said end effector includes a knot pusher at a distal end of said end effector.

10. An end effector according to claim 9 where in said knot pusher comprises a first notch in said first jaw and a second notch in said second jaw.

11. An end effector for a surgical instrument wherein said end effector comprises:
   first tissue grasping means having a first tissue grasping surface and a first exterior surface;
   second tissue grasping means having a second tissue grasping surface and a second exterior surface, said first tissue grasping surface being positioned opposite said second tissue grasping surface, said first and second tissue grasping means being adapted to move from an open position to a closed, tissue grasping, position;
   a first opening extending from said first tissue grasping surface to said first exterior surface;
   a second opening extending from said second tissue grasping surface to said second exterior surface, wherein only a portion of said first and said second openings overlap when said first and second tissue grasping means are in said closed position.

12. An end effector according to claim 11 further comprising:
   a first edge between said first tissue grasping surface and said first exterior surface, wherein said first opening extends from a central region of said first tissue grasping means to said first edge;
   a second edge between said second tissue grasping surface and said second exterior surface, wherein said second opening extends from a central region of said second tissue grasping surface to said second edge.

13. An end effector according to claim 12 wherein said end effector further includes a tying means at a proximal end.

14. A surgical instrument including a proximal end and a distal end, said instrument comprising:

a handle comprising first and second gripping members at said proximal end of said instrument;

an end effector comprising first and second jaw members at said distal end of said instrument;

an elongated tube connecting said handle to said end effector;

a connector within said tube connecting at least one of said gripping members to said jaw members; and a first slot in said first jaw member and a second slot in said second jaw member wherein said first and second slots are arranged such that only a portion of said slots overlap when said first and second jaws are closed.

15. A surgical instrument according to claim 14 wherein said first slot in said first jaw extends to a first side of said first jaw and said second slot in said second jaw extends to a first side of said second jaw.

16. A surgical instrument according to claim 15 wherein said instrument includes a retractable tying pin adjacent said proximal end of said end effector.

17. A surgical instrument according to claim 15 wherein said handle includes a trigger attached to said retractable tying pin through said tube.

18. A surgical instrument according to claim 17 wherein said retractable tying pin comprises a flexible rod.

19. A surgical instrument according to claim 18 wherein said first and second jaw members include notches at a distal end.

20. A method of using a surgical instrument including an end effector, said end effector comprising first and second jaw members wherein said first jaw member includes a first slot and said second jaw member includes a second slot, said first and second slots being arranged such that only a portion of said first and second slots overlap when said first and second jaws are closed, said method comprising the steps of:

closing said first and second jaws on tissue;

passing a surgical needle with a suture attached thereto through said tissue by passing said needle and suture through said overlapping portion of said first and second slots;

opening said first and second jaws and passing said suture through said first and said second slots;

twisting a portion of said suture around said end effector to create at least one suture loop; and grasping said suture and pulling said suture through said at least one loop.

21. A surgical instrument according to claim 20 wherein said wherein said instrument includes a tying pin adjacent said end effector and said method includes the steps of:

extending said tying pin prior to creating said suture loop; and retracting said tying pin prior to pulling said suture through said loop.

* * * * *